Figure 1:
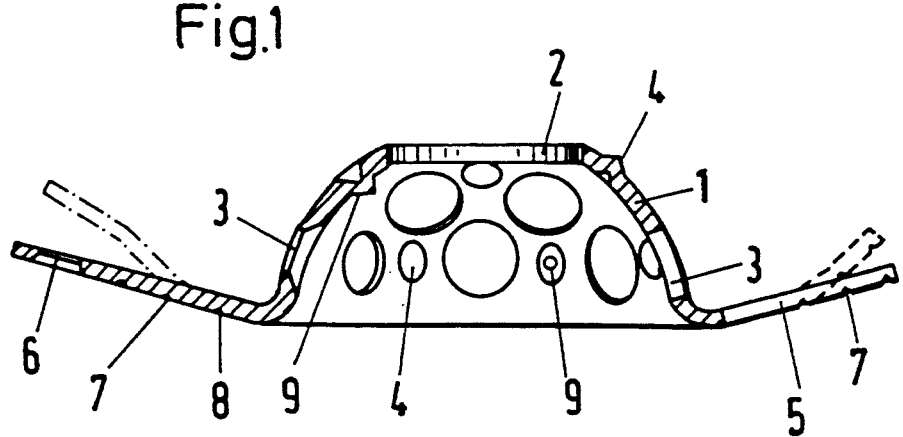

United States Patent [19]

Wagner et al.

[11] Patent Number: 5,314,490
[45] Date of Patent: May 24, 1994

[54] OUTER CUP FOR AN ARTIFICIAL HIPJOINT SOCKET

[75] Inventors: Heinz Wagner, Schwarzenbruck, Fed. Rep. of Germany; Roland Willi, Neftenbach, Switzerland

[73] Assignees: Sulzer Medizinaltechnik AG, Winterthur; Protek AG, Bern, both of Switzerland

[21] Appl. No.: 13,900

[22] Filed: Feb. 5, 1993

[30] Foreign Application Priority Data

Apr. 3, 1992 [EP] European Pat. Off. ........ 92810254.0

[51] Int. Cl.$^5$ .............................................. A61F 2/34
[52] U.S. Cl. ...................................................... 623/22
[58] Field of Search ............... 623/18, 22, 23; 606/72, 606/69, 71, 70

[56] References Cited

U.S. PATENT DOCUMENTS 3,955,567  5/1976  Richmond et al. .................. 626/69

FOREIGN PATENT DOCUMENTS 0242719  10/1987  European Pat. Off.
0290138  11/1988  European Pat. Off. .............. 606/69
2510057   7/1975  Fed. Rep. of Germany .
3027063   2/1982  Fed. Rep. of Germany .
8808699   8/1989  Fed. Rep. of Germany .

Primary Examiner—David Isabella
Attorney, Agent, or Firm—Townsend and Townsend Khourie and Crew

[57] ABSTRACT

An artificial hip joint socket for fastening to a pelvic bone includes a metallic outer cup for an artificial hipjoint socket forming a concavity for receiving a hip. This cavity terminates at an equatorial edge. Supporting flaps for fastening to said pelvic bone are provided at the equatorial edge of the metallic outer cup. These supporting flaps define holes drilled for bone screws to pass through and as openings for checking the clearance from the bone. The supporting flaps are provided with preset lines of grooves for enabling preferential bending of said flaps along said at least one of said preset lines of grooves to conform said supporting flaps and metallic outer cup to said pelvis. In the preferred embodiment, the preset lines of grooves run exclusively in the region of the supporting flaps undisturbed by defined holes in the flap. The preset lines of grooves are arranged on the outer surface of the flaps toward the pelvis. Round depressions are preferably provided at the intersections between said preset lines of grooves.

4 Claims, 1 Drawing Sheet

OUTER CUP FOR AN ARTIFICIAL HIPJOINT SOCKET

The invention is concerned with a metallic outer cup for an artificial hipjoint socket, which for fastening it into the pelvis at its equatorial edge is provided with supporting flaps which in turn exhibit drilled holes for bone screws to pass through.

Outer cups of the aforesaid kind are known, for example, from the EP-A-0 242 719 or the FR-A-2 595 241 (8603853); the supporting flaps of outer cups of such kind must frequently, especially in the case of repeat operations, be adapted intraoperatively to the pelvis which, particularly in the case of repeat operations, has often been damaged or has severely degenerated. In the case of the aforesaid known constructions, the operating surgeon frequently has difficulties in bringing the supporting flaps into the correct shape. The problem underlying the invention is therefore to facilitate the work of the operating surgeon in such cases and to facilitate exact adaptation of the supporting flaps to the bones; moreover it is to be possible through bending along the predetermined lines of grooves, to avoid the strength of the supporting flaps becoming inadmissibly reduced through uncontrolled bending, for example, across holes drilled for bone screws to pass through.

This problem is solved in the present invention by the supporting flaps being provided with predetermined lines of grooves. There exists thereby along these grooves a diminished resistance against plastic deformations so that the flaps preferably deform along the grooves.

In order to avoid inadmissible weakening of the supporting flaps, it is advantageous if the lines of grooves run exclusively in that region of the areas of the supporting flaps which is undisturbed by the drilled holes. Moreover it has proved useful if the groovelike lines are arranged on the outer surface of the flaps, i.e., that remote from the bone, since then their entire length is visible to the operating surgeon during trial insertion and adaptation of the outer cup.

In order to facilitate bending in regions of intersecting lines of grooves, round depressions may be provided at their intersections.

The invention is explained in greater detail below with the aid of embodiments in connection with the drawings.

Figure 2:
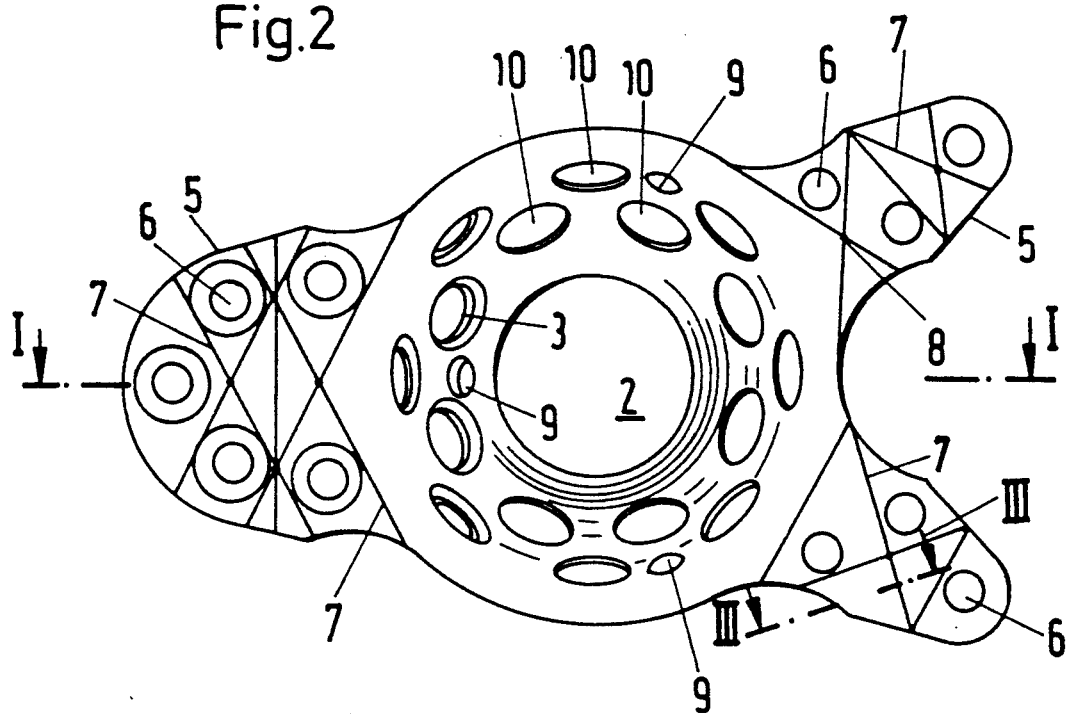
Figure 3:
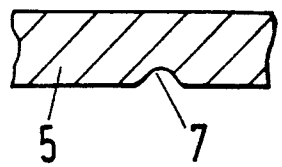

FIG. 1—shows in a section I—I from FIG. 2 an embodiment of the new outer cup;

FIG. 2—shows diagrammatically the plan in the direction of the polar axis on the "equator" of an outer cup in accordance with the invention; and FIG. 3—reproduces in a section IV—IV an enlarged section transversely to a line of grooves from FIG. 2.

The supporting or outer cup 1 (FIG. 1) for anchoring with bone cement, and consisting, for example, of titanium, is in its basic shape a hemisphere in the polar region of which a cap has been cut away so that there the cup 1 exhibits an opening 2. In the face of the cup, recessed openings 3 are provided for bone screws (not shown) to pass through, by means of which the cup 1 may be secured in the pelvis. Furthermore, the face of the cup exhibits inspection openings 10 in the form of drilled holes through which the distance from the bone tissue lying behind may be checked, and through which cement may be injected into the interstice from the bone tissue.

Knobs 4 are distributed on the outside of the face of the cup which, during the driving in of the outer cup, prelocate it on the bed of bone. Three knobs 9 are likewise fitted to the inside of the outer cup, which in the case of an inner cup which can be cemented in, keep it at such a distance that a bed of cement of constant thickness is generated between the two cups, in which the height of the knobs corresponds with the "gap" to be generated.

Along the equatorial edge of the cup 1, supporting flaps or tongues 5 are provided, which are likewise provided with drilled holes 6 for bone screws to pass through. These tongues 5 have the purpose of additionally locating the cup 1 on the pelvis. Since for doing that they must be adapted to the bone through bending, they are plastically deformable.

In order to guarantee bending in predetermined directions the supporting flaps 5 are traversed by predetermined lines of grooves 7 which are realized as groovelike depressions. They lie preferably on the outside, i.e., on the side of the flaps 5 remote from the bone. Moreover the lines of grooves 7 are so placed in the flaps that they do not cut across any of the perforations 6. Weakening of the strength of the flaps inadmissibly is thereby avoided and the deformed flaps are prevented from bending back during their location by bone screws.

At each intersection of two or more lines of grooves 7 around depression 8 is provided, through which multiple bending along intersecting lines of grooves 7— which during the operation is commonly effected by the operating surgeon—is facilitated.

Both the lines of grooves 7 and the depressions 8 are pressed into the surface of the supporting flaps 5 by means, for example, of press dies.

We claim:

1. An artificial hip joint socket for fastening to a pelvic bone comprising:
   a metallic outer cup for an artificial hipjoint socket forming a concavity for receiving a hip, said concavity terminating at an equatorial edge;
   supporting flaps for fastening to said pelvic bone provided at said equatorial edge of said metallic outer cup;
   said supporting flaps defining holes drilled for bone screws to pass through and as openings for checking the clearance from the bone; and,
   said supporting flaps provided with preset lines of grooves for enabling preferential bending of said flaps along said at least one of said preset lines of grooves to conform said supporting flaps and metallic outer cup to said pelvis.

2. An artificial hip joint socket for fastening to a pelvic bone outer cup as in claim 1 including:
   said lines of grooves run exclusively in region of the supporting flaps undisturbed by defined holes in said flap.

3. An artificial hip joint socket for fastening to a pelvic bone outer cup as in claim 1 including:
   said preset lines of grooves are arranged on the outer surface of the flaps toward said pelvis.

4. An artificial hip joint socket for fastening to a pelvic bone outer cup as in claim 1 including:
   at least one of said flaps defines preset lines of grooves which intersect; and,
   round depressions provided at the intersections between said preset lines of grooves.

* * * * *